United States Patent [19]

Machlowitz et al.

[11] 4,329,424

[45] May 11, 1982

[54] MACROSCOPIC METHOD FOR DETERMINING CYTOPATHIC EFFECTS IN VIRAL ASSAY

[75] Inventors: Roy A. Machlowitz, Glenside; William J. McAleer, Ambler; William J. Miller, North Wales, all of Pa.

[73] Assignee: Merck & Co., Inc., Rahway, N.J.

[21] Appl. No.: 881,299

[22] Filed: Feb. 27, 1978

Related U.S. Application Data

[63] Continuation-in-part of Ser. No. 610,501, Sep. 4, 1975, abandoned.

[51] Int. Cl.³ .................. C12Q 1/70; G01N 1/28; G01N 1/30; G01N 33/54
[52] U.S. Cl. .......................... 435/5; 424/7; 424/8; 424/12; 424/89; 435/7
[58] Field of Search ............... 424/3, 7, 8, 12, 89; 195/1.7, 1.8, 103.5 V; 435/5, 7

[56] References Cited

U.S. PATENT DOCUMENTS

| | | | |
|---|---|---|---|
| 3,309,274 | 3/1967 | Brilliant | 424/7 |
| 3,745,091 | 7/1973 | McCormick | 195/1.7 X |
| 3,889,014 | 6/1975 | Kinney | 424/3 X |

FOREIGN PATENT DOCUMENTS 1011641 7/1957 Fed. Rep. of Germany .......... 424/3

OTHER PUBLICATIONS

Hsiung, J. Immunol., vol. 78, Jun. 1957, pp. 128–136.
Cooke Engineering Co., Alex., Va. 22314, Automatic Diluter, Model 222-20-PU, Automatic Pipetter Model 222-1A, 1 page, adv.
Lennette, Diag. Proc. for Viral & Rickett. Dis., APHA, N. Y., 3rd ed., 1964, 78–85, 112–129.
Postlethwaite, Virology, vol. 10, 1960, pp. 466–482.
Finter, J. Gen. Virol., vol. 5, 1969, pp. 419–427.
Taketsy, Acta Microbiol. Acd. Sci. Hung., vol. 3, 1955, pp. 191–202.
Furesz, Cand. J. Microbiol., vol. 15, 1969, pp. 67–91.
Fenner, Med. Virol., Acd. Press, N. Y., 1970 (4th print.), pp. 35–37, 204–206, 349–353.

*Primary Examiner*—Anna P. Fagelson
*Attorney, Agent, or Firm*—Donald J. Perrella; Hesna J. Pfeiffer

[57] ABSTRACT

Semi-automated assays for viral infectivity and an assay for serum neutralizing antibody content are based on staining the cells and macroscopic reading of the cytopathic effect.

7 Claims, No Drawings

MACROSCOPIC METHOD FOR DETERMINING CYTOPATHIC EFFECTS IN VIRAL ASSAY

RELATED APPLICATION

This patent application is a continuation-in-part of copending U.S. patent application Ser. No. 610,501 filed Sept. 4, 1975 now abandoned.

BACKGROUND OF THE INVENTION

Prior art techniques for measuring viral infectivity and serum neutralizing antibody values have ranged from plaque techniques to semiautomated microtiter procedures. Typical of such prior art techniques are those described in the following publications:

Taketsy, Acta. Microbiol. Acad. Sci. Hung. 3:191–202, 1955;

Furesz et al., Can. J. Microbiology 15:67–71, 1969.

All of these procedures have the common disadvantage of requiring tedious time consuming microscopic examination of large numbers of tissue cultures by highly skilled personnel.

OBJECTS OF THE INVENTION

It is an object of the present invention to provide a faster and more economical assay for viral infectivity and for serum neutralizing antibody content. Another object is to provide an assay procedure which employs semi-automated techniques. A further object is to provide an assay which requires substantially less time of skilled personnel. Still another object is to provide a viral infectivity assay and serum neutralizing antibody assay which employs a stain-macroscopic procedure to determine end-points. These and other objects of the present invention will be apparent from the following description.

SUMMARY OF THE INVENTION

In the viral assay, dilutions of a virus preparation being assayed are mixed with a suspension of the appropriate tissue culture-grown cell suspension. Following incubation of the cells under appropriate conditions the cells are stained and then read without optical magnification.

In the serum neutralizing antibody content assay dilutions of a serum sample being assayed are mixed with a challenge virus. Following preincubation the serum/virus mixture is mixed with a suspension of the appropriate tissue culture-grown cell suspension. Following incubation of the cells under appropriate conditions, the cells are stained and read without optical magnification.

Uninfected wells show the even stain characteristic of normal cell cultures while wells containing infected cells show no stain at all or clear areas indicating destruction of cells, thereby permiting determination of the infectivity of the viral preparation being tested or the serum neutralizing antibody content.

DETAILED DESCRIPTION

The present invention is directed to a semi-automated quantitative assay for viral infectivity and for serum neutralizing antibody content.

In the viral assay dilutions of a virus preparation, preferably prepared electro-mechanically, are mixed with a suspension of the appropriate tissue culture-grown cell suspension which, preferably, has been automatically pipetted into the wells of a multi-well micro assay plate plate. Following incubation of the cells in the plate under appropriate conditions fluids are drained from the plate and the cells are stained with a protein stain and then read without optical magnification.

In the serum neutralizing antibody content assay, dilutions of a serum sample being assayed are mixed, preferably, electro-mechanically, with a challenge virus. To an appropriate tissue-culture grown cell suspension, which preferably has been automatically pipetted into the wells of a microtiter plate, is added the preincubated serum/virus mixture. Following incubation of the cells in the microtiter plate under appropriate conditions fluids are drained from the plates and the cells are stained with a protein stain and then read without optical magnification.

The viral assay of the present invention is applicable to any virus. It can be used for viruses which affect humans as well as for viruses which affect animals. By way of illustration without being limited thereby, some examples of viruses which can be used in the viral assay of the present invention are rubella, measles, mumps, herpes, polio, varicella and Marek's.

I. VIRAL ASSAY

A. Preparation of Assay Plates

Sterile tissue culture plates, transfer plates and lids are removed from their wrappers and assembled with the transfer plate in place in the tissue culture plate, both covered by the lid. The plates are marked with the cells being used, the date the assay is being started and an individual identification number on both lid and tissue culture plate. An assay sheet is prepared for each sample.

B. Preparation of Samples

Frozen samples and an aliquot of the house reference standard are thawed rapidly by being placed in a bath partially filled with cold tap water. The samples are thawed just prior to use and are kept in the cold water bath until removed for assay.

Lyophilized samples are reconstituted by adding required amount of diluent and kept in the cold water bath until removed for assay.

C. Preparation of Pipetter

A disposable plastic reservoir is placed in position in the base of the automatic pipetter. The pipetting head is partially placed in position in the unit after which a rubber vacuum diaphragm is positioned on top of the pipetting head. The diaphragm covered pipetting head is then moved into its final position and locked in place. Approximately 70 ml of diluting medium are then pipetted, using a sterile 100 ml volumetric pipette, into the reservoir which is refilled as required.

D. Preparation of Diluter

A disposable plastic reservoir is filled with sterile distilled water to a depth of approximately $\frac{3}{8}$ inch (sufficient for total immersion of the tips of the microdiluters).

The assembly of the microdiluters is removed from the diluter, immersed briefly in the water, touched down on a blotter and then each microdiluter is burned off in the flame of a Bunsen burner. The heated microdiluters are then dipped again into the water, touched down on the blotter and repositioned in the diluter.

After every plate, the assembly of microdiluters is removed, touched down on the blotter to remove residual virus suspension, then immersed in the water rinse and then blotted. (The cycle of immersion and blotting is repeated two more times). After every third plate, the assembly of microdiluters is removed, touched down on the blotter, immersed in water, blotted, flamed as described above, immersed and blotted. This same procedure is used at the end of the day's assays.

E. Titration of Samples

The transfer plate is removed from the tissue culture plate, transfer plate and lid assembly and placed in the transfer plate holder. (The lid is replaced atop the tissue culture plate.) The transfer plate holder is positioned in the automatic pipetter and 0.75 ml of diluent (0.025 ml drops 3 times) is added to each of the wells, typically 96 wells. The transfer plate holder is then removed from the pipetter. One drop (0.025 ml) of the sample being tested is carefully added, using a sterile pipette, to each of the 12 wells in Row A of the transfer plate. A fresh pipette is used for each sample. The transfer plate holder is then positioned in the automatic diluter which is then operated to perform seven 1:4 serial dilutions (0.6 $\log_{10}$ per dilution). The transfer plate is then removed from the transfer plate holder and placed back in the tissue culture plate and covered with the lid. If the sample is likely to have a titer greater than 4.2 $\log_{10}$, it should be diluted at least 10-fold below that level immediately before assay, using diluent.

When all the samples and reference standards have been diluted as above, the cell suspension is added as follows: the transfer plate is removed from the assembled unit and placed in the transfer plate holder and covered with the lid. The tissue culture plate of the unit is positioned in the automatic pipetter. (Just prior to this, the disposable reservoir containing diluent is replaced with a disposable reservoir containing the cell suspension at a concentration of from about 160,000 to about 260,000 cells per ml, preferably about 200,000 cells per ml. The pipetter is filled and emptied into the reservoir a few times to flush the unit.) A quantity, 0.075 ml, of the cell suspension is added to each of the wells in the tissue culture plate (0.025 ml drops 3 times).

The tissue culture plate is removed from the pipetter and the transfer plate is placed in it and then lifted out permitting transfer of the virus dilutions in the transfer plate to the cell suspension in the tissue culture plate. The transfer plate is discarded (to be autoclaved) and the lid is fitted carefully over the tissue culture plate. The other plates are treated similarly and stacked above one another, then placed in the incubator at the requisite incubating temperature, typically from about 30° to about 39° C., for the optimal incubation time for the virus.

At the end of the optimum incubation period for the particular virus, generally from about 7 to about 10 days after infection, the plates are removed from the incubator. The contents are removed, e.g. by a sharp snap of the wrist with the wells pointing downward. Each plate is, in turn, positioned in the automatic pipetter, the reservoir of which has previously been filled wih a protein stain-fixer which is effective to stain and fix the cells in the cell sheet substantially immediately, i.e., within a few minutes or less. An example of such a stain is Carbolfuchsin stain which stains and fixes the cells in the cell sheet within about 30 seconds.

The Carbolfuchsin stain may be used in concentrated form with a washing step following the staining, or in diluted form without a washing step following the staining. Then 0.075 ml of the stain is added to each well (0.025 ml drops 3 times). After a half-minute or more the stain is drained from the plate (as described above). The plate is immersed in a deep basin of tap water to rinse out excess stain and drained as before. (Rinsing may be eliminated by use of a more dilute stain). The plate is dried with a paper towel and covered with its lid.

F. Reading Assay

The plates are read macroscopically without optical magnification by exposure to a light source. A convenient method is to place the plates on a fluorescent light box. The wells showing CPE (cytopathic effect) are readily recognized by the areas showing no stain. Uninfected wells have a uniform red matrix. The infected wells are scored positive (+), the uninfected negative (−) on the assay sheet.

To calculate the titer of the sample, the infected and uninfected wells are summed up for each line of the assay plate using a calculation sheet. As indicated on that sheet, the titer is determined by a Reed-Muench or Karber calculation—briefly, the negatives are added going down, the positives added going up and the percent positive calculated at each dilution level as shown in the sample calculation.

II. SERUM NEUTRALIZING ANTIBODY ASSAY

A. Preparation of Assay Plates

Sterile tissue culture plates, transfer plates and lids are removed from their wrappers and assembled with the transfer plate in place in the tissue culture plate, both covered by the lid. The plates are marked with the cells being used, the date the assay is being started and an individual identification number on both lid and tissue culture plate. An assay sheet is prepared for each sample.

B. Preparation of Samples

The sera to be assayed are inactivated for 30 minutes at 56° C. and cooled to room temperature prior to use.

C. Preparation of Pipetter

A disposable plastic reservoir is placed in position in the base of the automatic pipetter. The pipetting head is partially placed in position in the unit after which a rubber vacuum diaphragm is positioned on top of the pipetting head. The diaphragm covered pipetting head is then moved into its final position and locked in place. Approximately 70 ml of diluting medium are then pipetted, using a sterile 100 ml volumetric pipette, into the reservoir which is refilled as required.

D. Preparation of Diluter

A disposable plastic reservoir is filled with sterile distilled water to a depth of approximately ⅜ inch (sufficient for total immersion of the tips of the microdiluters).

The assembly of microdiluters is removed from the diluter, immersed briefly in the water, touched down on a blotter and then each microdiluter is burned off in the flame of a Bunsen burner. The heated microdiluters are then dipped again into the water, touched down on the blotter and repositioned in the diluter.

After every plate, the assembly of microdiluters is removed, touched down on the blotter to remove residual virus suspension, then immersed in the water rinse and then blotted. (The cycle of immersion and blotting is repeated two more times). After every third plate, the assembly of microdiluters is removed, touched down on the blotter, immersed in water, blotted, flamed as described above, immersed and blotted. This same procedure is used at the end of the day's assays.

E. Titration of Samples

The transfer plate is removed from the tissue culture plate, transfer plate and lid assembly and placed in the transfer plate holder. (The lid is replaced atop the tissue culture plate.). The transfer plate holder is positioned in the automatic pipetter and 0.025 ml of diluent (one drop) is added to each of the 96 wells. The transfer plate holder is then removed from the pipetter. One drop (0.025 ml) of the sample (serum) being tested is carefully added, using a sterile pipette, to each of the two adjacent wells in Row A of the transfer plate and so on with five other sera being tested. The transfer plate holder is then positioned in the automatic diluter which is then operated to perform seven 1:2 serial dilutions. The transfer plate holder is then removed from the automatic diluter and positioned in an automatic pipetter, the reservoir of which is filled with the challenge virus suspension. On drop (0.025 ml) of the challenge virus suspension is then added to each well of the transfer plate. The transfer plate containing the diluted serum samples-virus mixtures is then removed from the transfer plate holder, placed on the tissue culture plate, covered with the lid and incubated for 1 hour at $36 \pm 1°$ C., 5% $CO_2$, 95% RH. At the end of the incubation period, the transfer plate is placed on the transfer plate holder and covered with the lid. The tissue culture plate is placed in the automatic pipetter the reservoir of which has been filled with an appropriate tissue culture suspension (typically 160,000 VERO cells per ml). 0.075 ml (3 drops) of the cell suspension is added for each of the wells in the tissue culture plate. The tissue culture plate is removed from the pipetter and the transfer plate is placed in it and then lifted out permitting transfer of the virus dilutions in the transfer plate to the cell suspension in the tissue culture plate. The transfer plate is discarded (to be autoclaved) and the lid is fitted carefully over the tissue culture plate. The other plates are treated similarly and stacked above one another, then placed in the incubator at the requisite incubating temperature, typically from about 30° to about 39° C., for the optimal incubation time for the virus.

At the end of the optimum incubation period for the particular virus, the plates are removed from the incubator. The contents are drained into a large pan by a sharp snap of the wrist the wells pointing downward. Each plate is, in turn, positioned in the automatic pipetter, the reservoir of which has previously been filled with a protein stain, e.g., Carbolfuchsin stain.

The Carbolfuchsin stain may be used in concentrated form with a washing step following the staining, or in diluted form without a washing step following the staining. Then 0.075 ml of the stain is added to each well (0.025 ml drops 3 times). After a half-minute or more the stain is drained from the plate (as described above). The plate is immersed in a deep basin of tap water to rinse out excess stain and drained as before. (Rinsing may be eliminated by use of a more dilute stain). The plate is dried with a paper towel and covered with its lid.

G. Serum Control

In order to ascertain whether the sera being tested are toxic to the cells used in the titration, another plate is prepared in which everything is the same except diluent is substituted for the challenge virus.

H. Virus Titration

The challenge virus used in this procedure is simultaneously assayed as described in the Viral Assay Procedure. For the dilution used in the serum neutralization assay the virus contains 20 to 50 $TCID_{50}$ per 0.025 ml.

The following examples illustrate the present invention without, however, limiting the same thereto. Unless indicated otherwise, all temperatures are expressed in degrees Celsius.

EXAMPLE 1

A. Tissue Culture

Cell suspensions of a rabbit kidney continuous cell line are prepared on the day they are to be used in the assay at 200,000 cells per ml in EMEM (Eagle's Minimum Essential Medium)+10% v/v fetal calf serum (not heat inactivated)+1% v/v of a 200 milli-molar solution of L-glutamine+0.05% of a 100 mg/ml solution of Neomycin (the L-glutamine is added just before use). Approximately 8 ml of cell suspension are required per sample. The cells are stirred until used.

B. Culture Medium

Diluting medium—EMEM+2% v/v fetal calf serum (not heat inactivated)+0.05% v/v of a 100 mg/ml solution of Neomycin+1% v/v of a 200 milli-molar solution of L-glutamine (the L-glutamine is added just before use).

C. Carbolfuchsin stain, concentrated 10 ml fuchsin stock (10 g basic fuchsin stirred 15 minutes in 95 ml warm 95% ethanol)
70 ml ethanol, 95%
320 ml phenol, 5% in water

D. Virus Samples

1. Frozen samples are stored at $-70°$ until tested.
2. Lyophilized samples are stored at $2°-5°$ until tested.
3. Frozen aliquots of a house reference standard virus suspension are stored at $-70°$ until tested. An aliquot is tested with each assay The assay plates, pipetter and diluter are prepared as indicated in the preceding Detailed Description. The samples of rubella virus, whether frozen or lyophilized, are prepared as indicated in section B of the Detailed Description. The sample is then added to the wells in row A of the transfer plate and the sample titrated, incubated and stained as in section E of the Detailed Description. The incubation is carried out at $32° \pm 1°$, 5% $CO_2$, 95% RH for 10 days. The staining is effected using concentrated Carbolfuchsin stain.

The plates are then read by being placed on the fluorescent light box and infected wells scored positive (+) and uninfected wells negative (−). The assay sheet is as follows:

|   | SAMPLE | | | | | | | | | | | |
|---|---|---|---|---|---|---|---|---|---|---|---|---|
|   | 1 | 2 | 3 | 4 | 5 | 6 | 7 | 8 | 9 | 10 | 11 | 12 |
| A | + | + | + | + | + | + | + | + | + | + | + | + |
| B | + | + | + | + | + | + | + | + | + | + | + | + |
| C | + | + | + | + | + | + | + | + | + | + | + | + |
| D | + | + | + | + | + | + | + | + | + | + | + | + |
| E | − | + | + | − | − | − | − | − | − | − | + | + |
| F | − | + | − | − | − | + | − | + | − | − | − | − |
| G | − | − | − | + | − | − | − | − | − | − | − | − |
| H | − | − | − | − | − | − | − | − | − | − | − | − |

The titer of the sample is calculated using the Reed-Muench or Karber technique using the following calculation sheet:

|   | $\log_{10}$ dilution of sample | P/N | N | P | % P |
|---|---|---|---|---|---|
| A | 0.6 | 12/0 |   |   |   |
| B | 1.2 | 12/0 |   |   |   |
| C | 1.8 | 12/0 |   |   |   |
| D | 2.4 | 12/0 | 0 | 20 | 100 |
| E | 3.0 | 4/8 | 8 | 8 | 50 |
| F | 3.6 | 3/9 | 17 | 4 | 19 |
| G | 4.2 | 1/11 | 28 | 1 | 3 |
| H | 4.8 | 0/12 | 40 | 0 | 0 |

The titer of this sample is 3.0 $\log_{10}$ per 0.025 ml.

EXAMPLE 2

Determination of Mumps Serum-neutralizing Antibody

A. Tissue Culture

Vero (a cercopithecous monkey kidney continuous cell line) cell suspensions are prepared on the day they are to be used in the assay at 160,000 cells per ml in Medium 199+10% v/v fetal calf serum (not inactivated)+0.05% v/v of a 100 mg/ml solution of Neomycin. Approximately 8 ml of cell suspension are required per plate. The cells are stirred until used.

B. Diluting Medium

Medium 199+20 ml per liter of agamma calf serum (inactivated)+85 ml per liter of 2.8% $NaHCO_3$+0.05% v/v of a 100 mg/ml solution of Neomycin.

C. Carbolfuchsin stain, dilute 10 ml fuchsin stock
175 ml ethanol, 95%
800 ml phenol, 5% in water

D. Serum samples

All samples are inactivated (56°, 30 minutes) prior to use.

E. Challenge Virus

MSD Mumps House Standard No. 3 diluted 1:20 with diluting medium just prior to use (or other suitable mumps virus preparation).

F. Procedure

The assay plates, pipetter and diluter are prepared as indicated in the preceding Detailed Description. A transfer plate, held in the transfer plate holder, is positioned in the pipetter, and one drop (0.025 ml) of diluting medium is added to each of the 96 wells. One drop (0.025 ml) of the serum being tested is added to each of two adjacent wells in row A of the transfer plate and so on with the five other sera being tested. The transfer plate is then positioned in the automatic diluter which, when operated, performs seven serial 1:2 dilutions of the sera being tested. The transfer plate, in the holder is then repositioned in the pipetter (just prior to this, the disposable reservoir has been filled with the suspension of the challenge virus) and one drop of challenge virus is added to each well. The transfer plate is then placed in the tissue culture plate, covered with the lid and kept in an incubator (36°±1°, 5% $CO_2$, 95% RH) for 1 hour. At the end of that period, the transfer plate is removed from the assembled unit and placed in the transfer plate holder and covered with the lid. The tissue culture plate of the unit is positioned in the automatic pipetter (just prior to this, the disposable reservoir has been filled with the cell suspension) and 0.075 ml of the cell suspension is added to each of the 96 wells in the tissue culture plate. The tissue culture plate is removed from the pipetter and the transfer plate is placed in the tissue culture plate and then lifted out, permitting transfer of the serum dilutions-virus mixtures in the transfer plate to the cell suspensions in the transfer plate. The transfer plate is discarded and the lid fitted over the tissue culture plate. Other plates are treated similarly and all plates are kept at 36°±1°, 5% $CO_2$ for 7 days. The plates are stained using the dilute Carbolfuchsin stain, drained but not washed and read as described in Example 1.

(2) Serum control

In order to ascertain whether the sera are toxic to the cells used in the titration another plate is prepared in which everything is the same except diluting medium is substituted for the challenge virus.

(3) Virus Titration

The challenge virus used in this procedure is simultaneously assayed, as described in Example 1. For the dilution used in the serum neutralization assay the virus contains 20 to 50 $TCID_{50}$ per 0.025 ml.

(4) Assay sheet

|   | Serum 1 | | Serum 2 | | Serum 3 | | Serum 4 | | Serum 5 | | Serum 6 | |
|---|---|---|---|---|---|---|---|---|---|---|---|---|
|   | 1 | 2 | 3 | 4 | 5 | 6 | 7 | 8 | 9 | 10 | 11 | 12 |
| A | + | + | − | − | − | − | − | − | + | + | − | − |
| B | + | + | − | − | + | + | − | − | + | + | − | − |
| C | + | + | − | − | + | + | − | − | + | + | − | − |
| D | + | + | − | − | + | + | − | − | + | + | + | + |
| E | + | + | + | + | + | + | − | − | + | + | + | + |
| F | + | + | + | + | + | + | − | − | + | + | + | + |
| G | + | + | + | + | + | + | + | + | + | + | + | + |
| H | + | + | + | + | + | + | + | + | + | + | + | + |

Calculation of results

|   | Dilution | Serum 1 | Serum 2 | Serum 3 | Serum 4 | Serum 5 | Serum 6 |
|---|---|---|---|---|---|---|---|
| A | 1:2 | 2/0 | 0/2 | 0/2 | 0/2 | 2/0 | 0/2 |
| B | 1:4 | 2/0 | 0/2 | 0/2 | 2/0 | 2/0 | 0/2 |
| C | 1:8 | 2/0 | 0/2 | 2/0 | 0/2 | 2/0 | 0/2 |
| D | 1:16 | 2/0 | 0/2 | 2/0 | 0/2 | 2/0 | 2/0 |
| E | 1:32 | 2/0 | 2/0 | 2/0 | 0/2 | 2/0 | 2/0 |
| F | 1:64 | 2/0 | 2/0 | 2/0 | 0/2 | 2/0 | 2/0 |
| G | 1:128 | 2/0 | 2/0 | 2/0 | 2/0 | 2/0 | 2/0 |
| H | 1:256 | 2/0 | 2/0 | 2/0 | 2/0 | 2/0 | 2/0 |
|   | Titer | 1:2 | 1:16 | 1:2 | 1:64 | 1:2 | 1:8 |

EXAMPLE 3

A herpes virus neutralization assay involving 192 sera, was performed following the procedure of Example 2. The total time involved was two man days. The test required 48 auto-CPE plates and about 500 ml of reagents. To perform the same test by the standard plaque assay (PFU) would have required 20 man days of work and would have required 2,000 CPE days and about 2,500 ml of reagents.

What is claimed is:

1. A method for quantitatively determining cytopathic effect in a cell culture comprising the steps of
   adding a series of virus dilutions to a cell suspension in the wells of a multi-well microassay plate,
   incubating the resulting infected cell sheets in the presence of an oxygen-$CO_2$ atmosphere and in the absence of an immobilizing or sealing overlay,
   staining the cell sheets at from about 7 to about 10 days after mixing with a protein stain effective to stain and fix the cell sheets substantially immediately whereby the evenly stained areas indicate absence of cytopathic effect and unstained areas indicate presence of cytopathic effect,
   exposing the stained cell sheets to a light source, and
   scoring each cell sheet for presence or absence of cytopathic effect by inspection for presence or absence of light passing through an unstained area, the inspection being effected without optical magnification and without counting individual foci of infection.

2. A method according to claim 1, wherein the protein strain is carbolfuchsin stain.

3. A method according to claim 1 wherein excess protein stain is removed after staining.

4. A method according to claim 1 wherein the virus is rubella.

5. A method according to claim 1 wherein the virus is mumps.

6. A method according to claim 1 wherein the virus is measles.

7. A method according to claim 1 wherein the virus is herpes.

* * * * *